United States Patent [19]

Uchiyama et al.

[11] 4,123,170
[45] Oct. 31, 1978

[54] APPARATUS FOR DETECTING DEFECTS IN PATTERNS

[75] Inventors: Yasushi Uchiyama, Yokohama; Daikichi Awamura, Kawasaki, both of Japan

[73] Assignee: Nippon Jido Seigyo, Ltd., Kawasaki, Japan

[21] Appl. No.: 746,584

[22] Filed: Dec. 1, 1976

[30] Foreign Application Priority Data

Nov. 26, 1975 [JP] Japan .................. 50-141394

[51] Int. Cl.² ........................................ G01B 11/00
[52] U.S. Cl. ................................ 356/167; 356/168
[58] Field of Search .................. 356/167, 168; 250/563

[56] References Cited

U.S. PATENT DOCUMENTS

| | | | |
|---|---|---|---|
| 3,379,829 | 4/1968 | Gambrell et al. | 250/563 |
| 3,811,011 | 5/1974 | Hardy et al. | 356/167 |
| 3,944,369 | 3/1976 | Cuthbert et al. | 356/168 |

Primary Examiner—John K. Corbin
Assistant Examiner—R. A. Rosenberger
Attorney, Agent, or Firm—Stevens, Davis, Miller & Mosher

[57] ABSTRACT

An apparatus for detecting defects in patterns, particularly defects in chip patterns of photomasks used for manufacturing semi-conductor integrated circuits comprises means such as a flying spot scanner for producing a scanning light spot, an optical system for projecting said scanning light spot simultaneously on to identical portions of two patterns to be compared with each other, said patterns being placed on a carrier stage, first and second photoelectric converters, each converter receiving the light spot passing through or reflected from a respective pattern to produce an output electrical signal; and an electric circuit for receiving the output signals from said first and second photoelectric converters and subtracting one of them from the other to produce a difference signal which represents detected defects in the patterns. The electric circuit means further comprise a delay circuit for delaying before subtraction one of the signals from the photoelectric converters or delaying said difference signal by a predetermined time period so as to delete pseudo-defects in the patterns.

10 Claims, 18 Drawing Figures

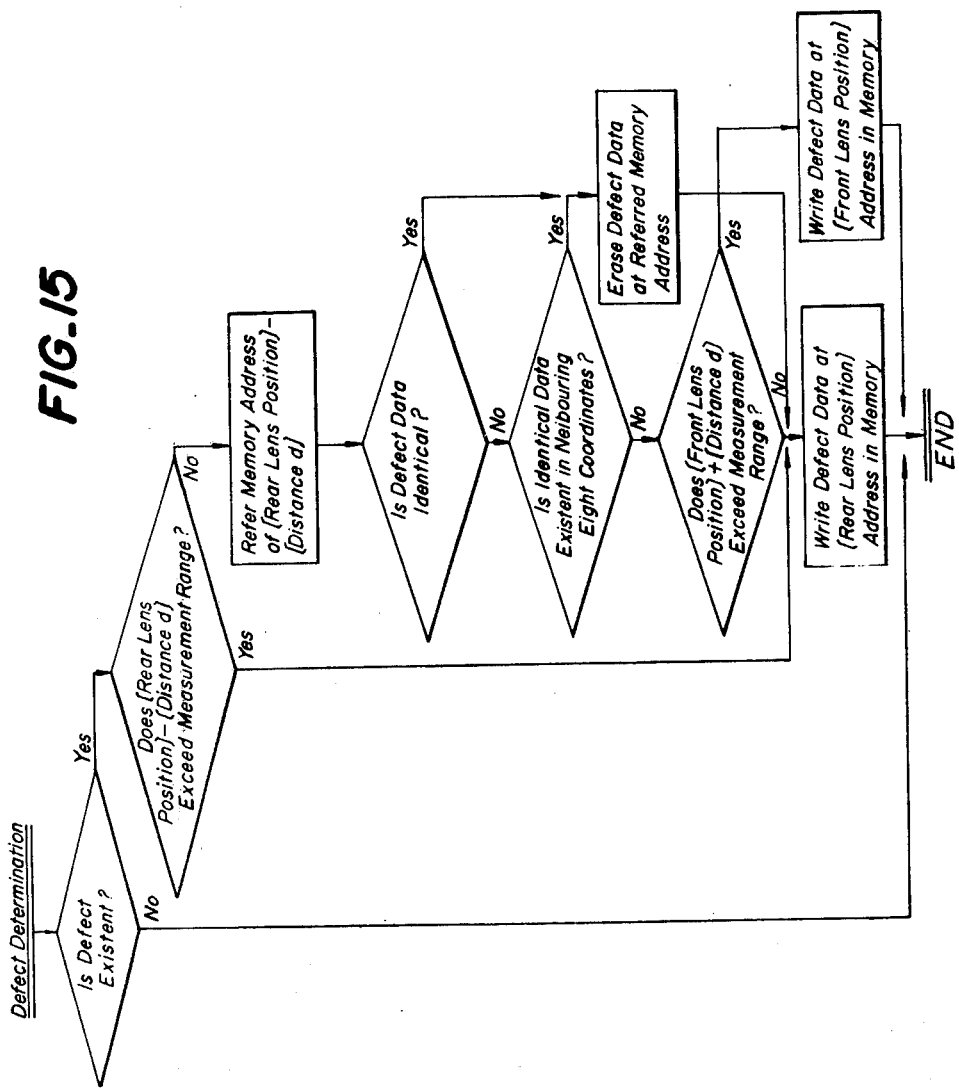

APPARATUS FOR DETECTING DEFECTS IN PATTERNS

BACKGROUND OF THE INVENTION

1. Field of the Invention

The invention relates to an apparatus for detecting defects in patterns, particularly defects in chip patterns of photomasks for use in manufacturing semi-conductor integrated circuits.

2. Description of the Prior Art

In the processes of manufacturing the integrated circuits there is a process for photoetching a silicon wafer. In this process the mask having a desired pattern is placed on a photo-lacquer layer applied on the silicon wafer and the photo-lacquer layer is irradiated by visible light or ultra-violet ray through the mask. Then the silicon wafer is selectively photoetched in accordance with the mask pattern. The defects in the mask having the pattern printed thereon might affect the yield of the manufactured integrated circuits. The mask is formed by depositing a metal film such as chromium on a glass plate having a sufficiently flattened surface and then by printing a desired pattern on the surface. If there are pin holes in the metal film, the printed pattern might have defects. The present inventors have developed an apparatus for detecting automatically such pin holes in the metal film of the mask pattern with high accuracy.

The photomask has various defects in its pattern as well as the pin holes. The defect detecting apparatus according to the present invention is particularly suitable to detect such defects in the printed pattern of the photomask.

FIG. 1 shows schematically a photomask 1 which is used for manufacturing the semiconductor integrated circuits. In the mask 1 there are formed a number of identical chip patterns 3 which are divided by a number of orthogonal scribe lines 2.

FIG. 2 is a microscopic image of a part of the chip pattern 3. This part of the pattern has no defect and thus is a perfect one. The pattern is composed of transparent portions 4 and opaque portions 5. FIG. 3 is also a microscopic image of the corresponding part of another pattern which includes various defects. Portions A and B are residual parts of the metal film. At the portion A the residual part bridges two adjacent lands which should be separated from each other. Thus this residual portion A should be detected as a real defect. While the other residual portion B exists in a space and in most cases this portion B might not injure the integrated circuits. At a portion C a part of a land is lacking. However, this land is not completely separated and thus this portion C might not affect the integrated circuits. At a portion D a land is completely cut away and this causes serious influence on the integrated circuits.

Up-to-date there have been developed the following methods for detecting the above mentioned defects in the mask pattern.

(1) The mask is inspected by means of a microscope so as to find the defects. In general the pattern is formed by straight lines which intersect perpendicularly with each other, whilst the most defects have irregular shapes as shown in FIG. 3. Therefore the defects can be found in a relatively easy manner. However, this method requires a lot of time and labor work and thus is not suitable for detecting the defects in the photomask used in manufacturing the integrated circuits which has a number of chip patterns.

(2) As shown in FIG. 4 a sample mask 7 which has a perfect pattern is prepared and images of this sample mask 7 and the mask 6 to be tested are inspected in a superimposed manner. In this case the image of the mask 6 to be tested is colored in red and the image of the sample mask 7 is colored in green which is complementary to red. For this purpose there is arranged red color light source 9 and the mask 6 to be tested is irradiated by red light emitted from the source 9. The red light passing through the mask 6 is made incident on an inspection eye 14 by means of an objective 10, a mirror 11, a half mirror 12 and an eye piece 13. The sample mask 7 is illuminated by a green light source 15 and the green light passing through te sample mask 7 is made incident upon the inspection eye 14 by means of the objective 16, a mirror 17, a half mirror 18 and the eye piece 13. When the sample mask 7 having no defect as shown in FIG. 2 and the test mask 6 having the defects as illustrated in FIG. 3 are inspected in a superimposed manner, the portions A and B are seen in green, because in these portions only the green light from the sample mask 7 reaches the inspection eye 14. The portions C and D are seen in red, because in these portions only the red light from the mask 6 reaches the eye 14. The transparent portion other than the portions A, B, C and D can be seen in white, because in the transparent portion both the green and red light rays from the masks 6 and 7, respectively reach simultaneously the inspection eye 14. The opaque portion 5 is seen, of course in black. The defect portions are seen in green or red and the portions having no defect are seen in black or white. Thus the defects can be found in a simpler manner. The mask used in manufacturing the integrated circuits have formed therein a number of identical chip patterns and in order to check such a mask it is necessary to arrange the mask 6 to be tested and the sample mask 7 on a same carrier stage 19 and to move this carrier stage 19 slightly so as to check the successive chip patterns. In case of inspecting the two images of the masks 7 and 6 in the superimposed manner two images must be aligned accurately. If there is an error in this alignment it is impossible to detect the defects accurately. In particular when the two masks 6 and 7 are placed on the same table 19, the masks must be aligned with X and Y directions of the movement of the table. If there is an error in this alignment, the error in superimposition of the two images will increase in accordance with the movement of the table 19. A play in the carrier table 19 also affects the superposition of the two images. Moreover since this method is effected with the naked eye, the inspector might be tired and errors caused by the human beings could not be avoided. Also long time period is required for inspection.

(3) Electric signals corresponding to a sample pattern which does not include a defect have been previously stored in a record medium such as a magnetic tape or memory elements with using an electronic computer. The image of the mask to be tested is picked up by means of a microscopic television camera to produce a video signal. This video signal is compared with the previously stored signal of the sample pattern so as to detect the defects in the checked mask. This method has an advantage that the defects can be detected automatically without using the eyes of the human beings. However an apparatus for carrying out such a method is very large and complicated and thus the apparatus becomes quite expensive.

In order to avoid the disadvantages mentioned above the inventors have designed an apparatus comprising a single camera tube on which images of identical portions of two patterns to be checked are focussed in a superimposed manner and defects in the patterns are detected by detecting an amplitude of the output video signal from the camera tube. In this apparatus the defects are represented as gray tones in the video signal and the gray tones are detected by means of an amplitude limiter. However the accuracy of the defect detection was low, because the fluctuation of the amplitude of the video signal is large. In order to obviate this disadvantage the inventors have further developed a method in which use is made of two camera tubes on each of which a respective image of the two patterns is formed and defects in the patterns are detected by comparing two output video signals from the two camera tubes. In this method the accuracy of the defect detection could be raised to a great extent as compared with the method in which only the single camera tube is used. However it has been found that it is quite difficult to make the operations of the two camera tubes identical with each other. Moreover in case of using the camera tube the carrier table on which the masks to be compared are placed must be transported intermittently due to the residual image effect of the camera tube. This results in a very complicated driving mechanism for the carrier table. The operation speed of the camera tube is rather slow and a time period of 70 to 100 ms is required for checking each field of view. Therefore a quite long time is required for detecting the defects in a number of patterns of the mask.

SUMMARY OF THE INVENTION

The present invention has for its object to provide a defect detecting apparatus which can avoid the above mentioned disadvantages and can detect rapidly and easily the defects in the pattern with very high accuracy.

According to the present invention an apparatus for detecting defects in a pattern comprises means for producing a scanning light spot; an optical system for projecting the scanning light spot simultaneously onto identical portions of two patterns to be compared with each other; first and second photoelectric converters each for receiving the scanning light spot passing through or reflected from a respective pattern to produce output electrical signal; and electric circuit means for subtracting one of said output signals supplied from the first and second photoelectric converters from the other output signal to produce a defect signal representing detected defects in the patterns.

BRIEF DESCRIPTION OF THE DRAWINGS

FIG. 15 is a flow chart illustrating the operation of the apparatus of FIG. 14.

DESCRIPTION OF THE PREFERRED EMBODIMENTS

Figure 5:
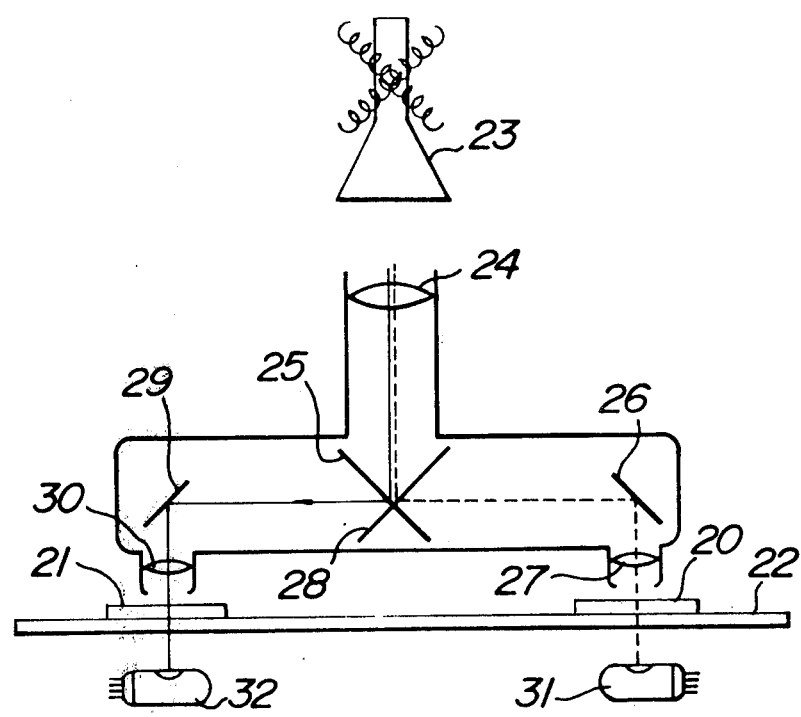
FIG. 5 is a schematic view showing an embodiment of an optical system of a defect detecting apparatus according to the invention.

FIG. 5 shows diagrammatically an embodiment of an optical system of a defect detecting apparatus according to the invention. In this embodiment a mask 20 to be tested and a sample mask 21 having no defect are placed on a single carrier table 22. There is provided a flying spot cathode ray tube 23 and an image of a scanning raster formed by the flying light spot is focussed on the mask 20 by means of a lens 24. a half mirror 25, a mirror 26 and a lens 27 and on the mask 21 by means of the lens 24, a half mirror 28, a mirror 29 and a lens 30. The light passing through the mask 20 is received by a first photoelectric converter 31 and the light through the mask 21 is received by a second photoelectric converter 32. In this case the raster image of the flying spot scanner 23 should be projected on identical pattern portions of the masks 20 and 21. Therefore if the mask 20 does not include a defect in the related pattern portion, the electric output signals from the photoelectric converters 31 and 32 become identical with each other. But if the mask 20 has a defect, the two output signals are different from each other. Therefore by comparing these output signals the defects in the pattern on the mask 20 can be detected with the high accuracy.

In the above embodiment since the mask 20 and the sample mask 21 are placed on the same carrier table 22 and are moved in the orthogonal X and Y directions, the two masks have to be aligned accurately in the X and Y directions. If the two masks 20 and 21 are not aligned correctly or the carrier table 22 has a play, the scanned pattern portions of the masks 20 and 21 become different from each other with the movement of the carrier table 22 and thus the accurate defect detection could not be effected.

Figure 6:
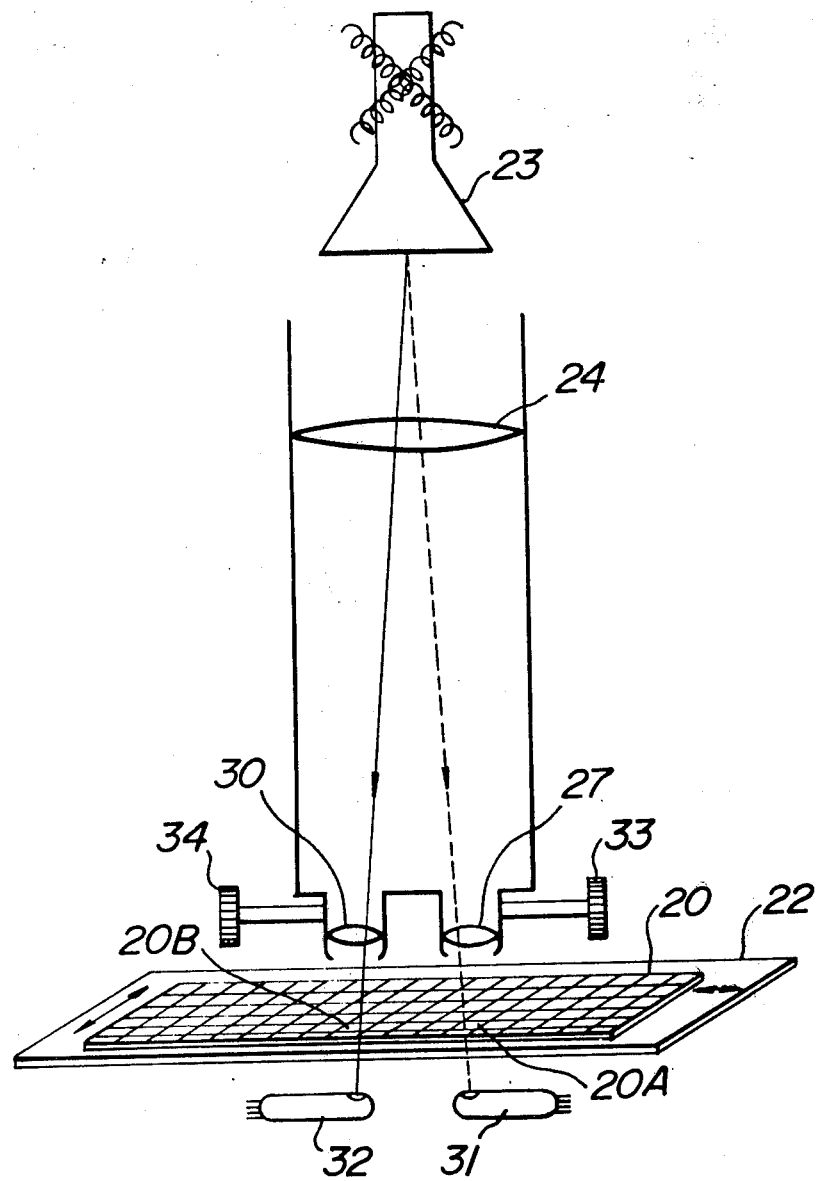
FIG. 6 is a schematic view illustrating another embodiment of the optical system of the defect detecting apparatus according to the invention.

FIG. 6 shows another embodiment of the optical system of the defect detecting apparatus according to the invention. In this embodiment the disadvantage just mentioned above can be deleted. In FIG. 6 the same elements as those shown in FIG. 5 are denoted by the same reference numerals. In FIG. 6 only the mask 20 to be checked is placed on the carrier table 22. A scanning raster image of the flying spot scanner tube 23 is focussed on a part of a pattern 20A of the mask 20 by means of a common lens 24 and a first lens 27 and on a corresponding part of a pattern 20B which is near the pattern 20A by means of the common lens 24 and a second lens 30. In order to inspect the identical portions of the patterns 20A and 20B a distance between optical axes of the lenses 27 and 30 can be adjusted by means of adjusting handles 33 and 34. In the present embodiment the accuracy of the defect detection is little affected by the play of the carrier table 22, because the two patterns 20A and 20B are situated quite near.

Figure 3:
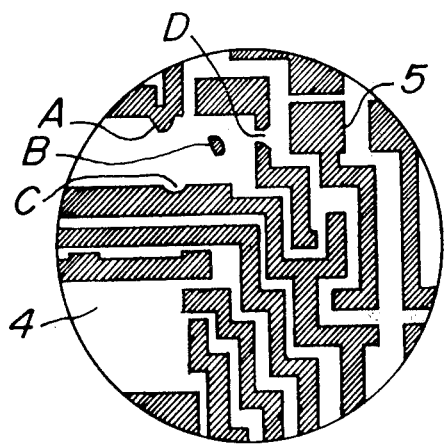
FIG. 3 is also a microscopic image of the same part of a photomask which includes various defects.
Figure 4:
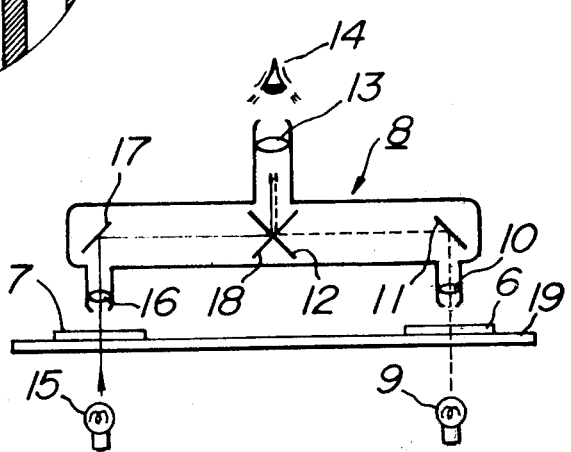
FIG. 4 is a schematic view illustrating a known defect detecting apparatus.
Figure 7:
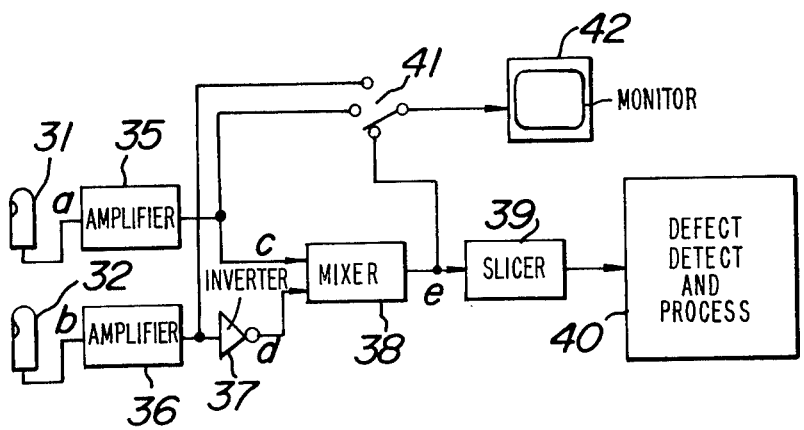
FIG. 7 is a block diagram showing an embodiment of electric circuit means of the defect detecting apparatus according to the invention.
Figure 8:
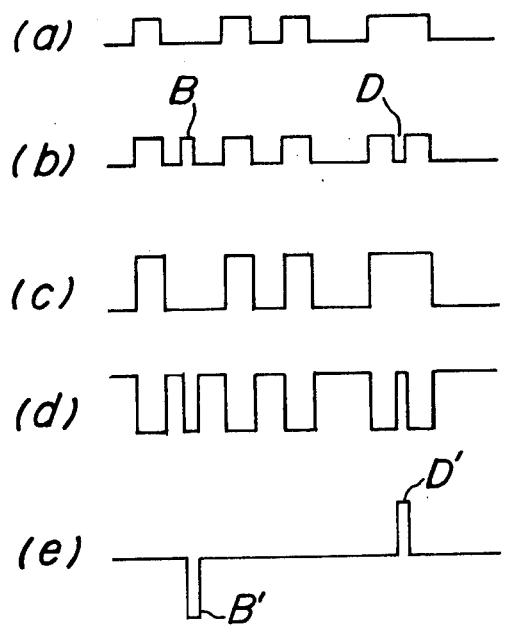
FIGS. 8(a) to 8(e) are waveforms for explaining the operation of the circuit means of FIG. 7.

FIG. 7 is a circuit diagram illustrating an embodiment of electrical circuit means of the defect detecting apparatus according to the invention. FIG. 8 is waveforms at various points of the circuit of FIG. 7. FIG. 8a shows a waveform of an output signal from the first photoelectric converter 31 which receives the scanning light spot passing through the pattern 20A and FIG. 8b illustrates a waveform of an output signal from the second photoelectric converter 32 which receives the scanning light spot passing through the pattern 20B. It is now assumed that one of the patterns 20A does not include a defect, but the other pattern 20B has defects. A pulse B in the waveform of FIG. 8b is produced by the defect B shown in FIG. 3 and a pulse D corresponds to the defect D in FIG. 3. The signal supplied from the first photoelectric converter 31 is amplified by an amplifier 35. The signal from the second photoelectric converter 32 is also amplified by an amplifier 36 and is then inverted by an inverter 37. The amplified signal (FIG. 8c) from the amplifier 35 and the amplified and inverted signal (FIG. 8d) from the inverter 37 are supplied to a mixer 38. An output signal from the mixer 38 is shown in FIG. 8e. As shown in the drawing the level of the mixer output signal corresponding to portions with no defect appears as a zero level, but the signal level differs from zero at portions of defects to produce pulses B' and D'. These defect pulses B' and D' have opposite polarities. These pulses are supplied through a slicer 39 to a defect detection and process circuit 40. The output defect signal from the mixer 38 may be supplied to a monitor 42 through a switch 41 so as to inspect the condition of superimposition of the two patterns 20A and 20B. That is the user can adjust the handles 33 and 34 while inspecting the superimposed images of the patterns 20A and 20B on the monitor 42 and the two images can be registered completely. Moreover in order to inspect in detail any one of the images of the patterns 20A and 20B, any one of the output signals from the amplifiers 35 and 36 may be supplied to the monitor 42 through the switch 41.

Figure 1:
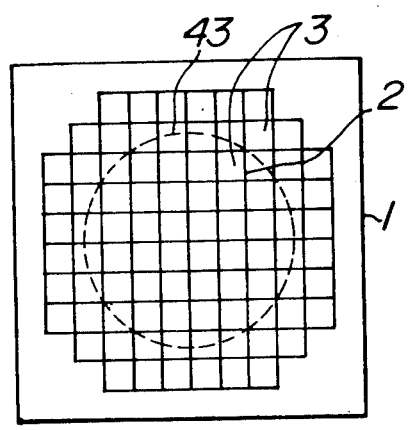
FIG. 1 is a plan view showing a photomasks used for manufacturing integrated circuits.
Figure 2:
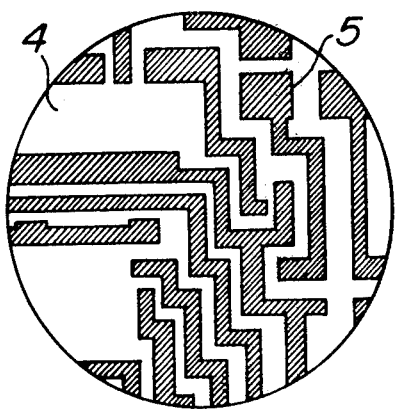
FIG. 2 is a microscopic image of a part of a photomask which does not include any defect.

In the embodiment shown in FIG. 6 the two patterns 20A and 20B of the same mask 20 to be checked are compared with each other. This is based on the fact that the mask has a number of identical patterns and a probability that the same defects are existent in these patterns is very small, and thus the defects can be detected very accurately without using the sample mask having the perfect patterns. In this method the number of the comparisons of the patterns situated near the peripheral portion of the mask is small and the detection accuracy for these peripheral patterns might be reduced. However, in general only the patterns in the mask which are enclosed by a dotted circle 43 in FIG. 1 are used in manufacturing the semiconductor integrated circuits, and the peripheral patterns are not used. Thus no serious problem arises.

In the above embodiment the signal representing the pattern 20B (FIG. 8d) is subtracted from the signal representing the pattern 20A (FIG. 8c). In addition to this the latter signal of FIG. 8c may be subtracted from the former signal of FIG. 8d so as to produce pulse signals having the opposite polarity to that shown in FIG. 8e. These two pulse signals are supplied to a rectifying circuit to produce a pulse signals having, for example a positive polarity. When such a pulse signal is supplied to the monitor 42, the defects are displayed as white images on the monitor screen. In stead of such measure the pulse signal of FIG. 8e may be supplied to a full-wave rectifying circuit.

In the explanation hereinbefore it is assumed that the defects have relatively large areas and should be detected as true defects. In the practical defect detection process, there are produced a number of very small defects due to the registration error of the patterns 20A and 20B and minute defects in these patterns. It is quite undesirable that these small defects are detected as true defects. These small defects should be discarded as pseudo- or false defects.

Figure 9:
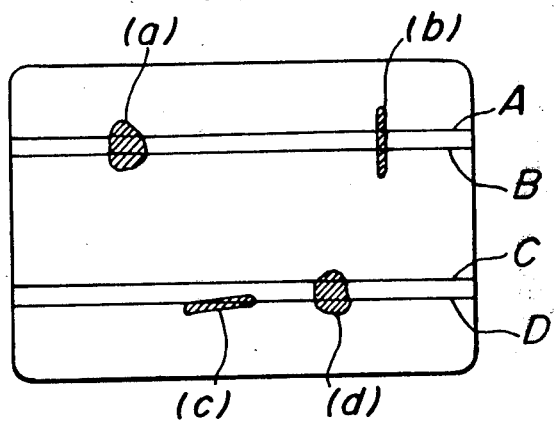
FIG. 9 is a schematic view of a monitor screen for illustrating various kinds of defects.

FIG. 9 illustrates four kinds of defects displayed on the monitor screen. The defects (a) and (d) should be identified as true defects, but the defects (b) and (c) should be discarded as pseudo-defects.

Figure 10:
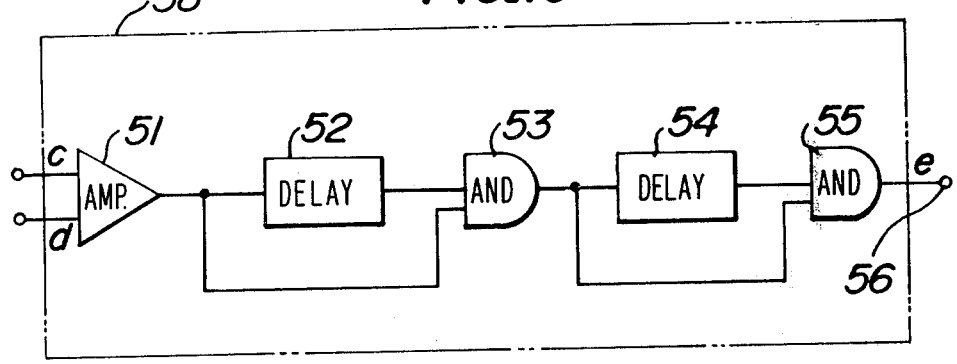
FIG. 10 is a circuit diagram of a defect defecting and processing circuit according to the invention.

FIG. 10 is a circuit diagram depicting an embodiment of a defect identifying circuit 38 which can reject the pseudo-defects. The signals c and d from the amplifier 35 and the inverter 37 (see FIG. 7), respectively are supplied to a mixing amplifier 51 so as to produce a sum signal of these input signals c and d. It should be noted that this sum signal is equivalent to a difference signal between the output signals from the first and second photoelectric converters. The sum signal may be displayed on the monitor screen as shown in FIG. 9. The output sum signal from the amplifier 51 is supplied through a first delay circuit 52 having a delay time of 0.08 $\mu$ seconds to one input of a first AND gate 53. To the other input of this AND gate 53 is supplied directly the sum signal. An output signal from the first AND gate 53 is supplied through a second delay circuit 54 having a delay time of 53.3 $\mu$ seconds to one input of a second AND gate 55, to the other input of which is supplied directly the output signal from the first AND gate 53. An output of the second AND gate 55 is connected to an output terminal 56 of the defect identifying circuit 38.

Figure 11:
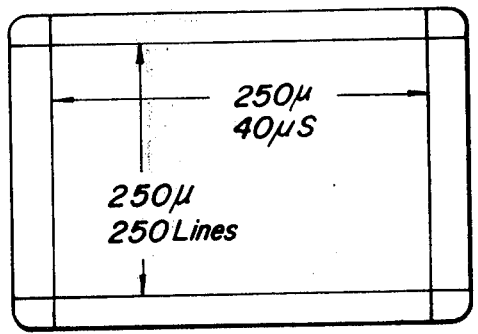
FIG. 11 is a plan view of the monitor screen for explaining dimensions of the monitor screen.

The reason for selecting the delay times of the first and second delay circuits 52 and 54 to 0.08 $\mu$ seconds and 53.3 $\mu$ seconds, respectively is as follows. The raster scanning system of the present flying spot scanner is set as follows. The number of scanning lines per field is 625 lines, adapting 2:1 interlace and the number of fields per second is 60. FIG. 11 shows diagrammatically a raster thus formed. As shown in FIG. 11 a length of 250 microns in the horizontal direction corresponds to a time period of 40 micro seconds and a length of 250 microns in the vertical direction corresponds to 250 scanning lines. That is to say during the time period of 40 micro seconds in the horizontal scanning period of 53.3 micro seconds the portion of the mask having a length of 250 microns in the horizontal direction is picked-up and during 250 scanning line period in 312.5 scanning line period a portion of the mask having a length of 250 microns in the vertical direction is picked-up. A magnification of the lenses and the electron beam deflection is so determined that the above conditions can be satisfied. In the present embodiment it is assumed that pseudo-defects are rejected by deleting or slicing off the contour by 1 micron in the horizontal and vertical directions. Therefore in the horizontal direction the defect image is cut off by 0.5 microns at left and right edges and a length of 0.5 microns corresponds to a time period of 0.08 micro seconds. A length of 1 micron in the vertical direction corresponds to one horizontal scanning period of 53.3 micro seconds. In accordance with the above mentioned calculation the delay time of the first delay circuit 52 is determined to 0.08 micro seconds and that of the second delay circuit 54 is set to 53.3 micro seconds.

Figure 12:
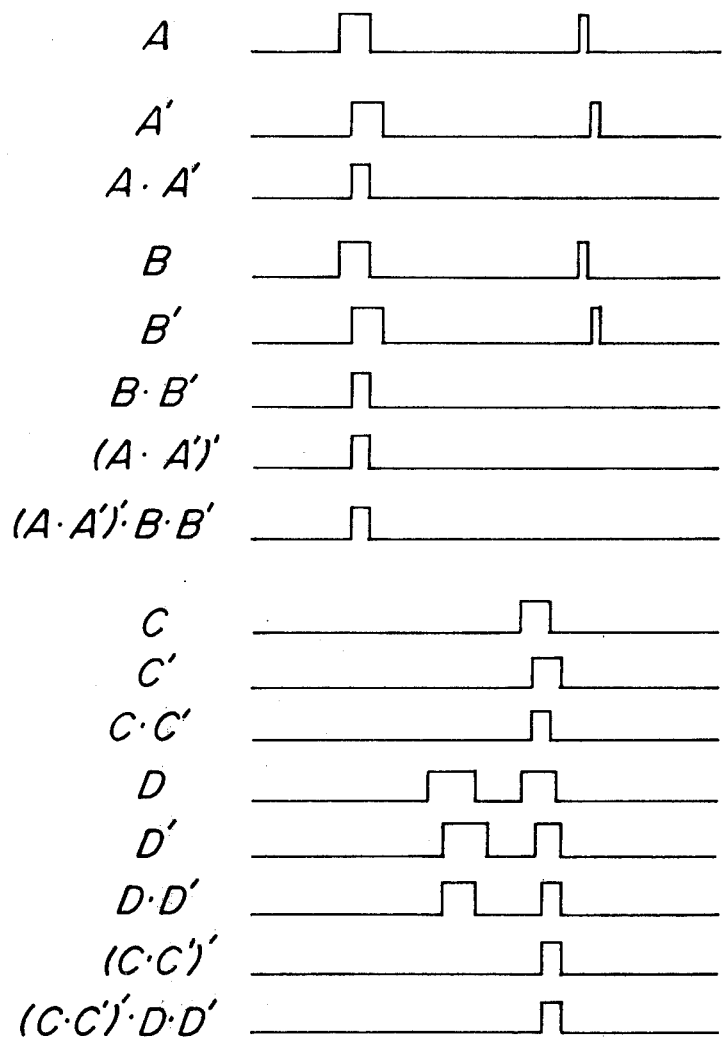
FIG. 12 shows various waveforms for explaining the operation of the defect detecting and processing circuit of FIG. 10.

Now the operation of the defect identification circuit 38 will be explained with reference to waveforms illustrated in FIG. 12. A signal A in FIG. 12 can be obtained by simultaneously scanning the patterns 20A and 20B (FIG. 6) by the scanning line A shown in FIG. 9 and then by subtracting the signal a supplied from the first photoelectric converter 31 from the signal b from the second photoelectric converter 32. A signal A' shown in FIG. 12 is obtained by delaying the signal A by 0.08 micro seconds by means of the first delay circuit 52. These signals A and A' are supplied to the first AND gate 53 so as to obtain a signal A·A' illustrated in FIG. 12. Signals B, B' and B·B' in FIG. 12 can be produced by processing in the same manner signals from the photoelectric converters 31 and 32 when the patterns are scanned by the scanning line B shown in FIG. 9.

A signal (A·A')' can be obtained by delaying the signal A·A' by 53.3 micro seconds by means of the second delay circuit 54. When this signal (A·A')' and the signal B·B' are applied to the second AND gate 55, a signal (A·A')'·B·B' shown in FIG. 12 can be obtained at the output terminal 56. This output signal represents the true defect (a) shown in FIG. 9, but the pseudo-defect (b) is completely deleted from the output signal.

Signals C and D of FIG. 12 can be obtained in relation to the scanning lines C and D shown in FIG. 9, respectively. The signal C is delayed by 0.08 micro seconds by means of the first delay circuit 52 and the delayed signal C' and the non-delayed signal C are supplied to the first AND gate 53 so as to produce a signal C·C' illustrated in FIG. 12. The signal D is treated in the same manner and the AND gate 53 produces a signal D·D' in FIG. 12. The signal C·C' is further delayed by 53.3 micro seconds and the delayed signal (C·C')' and the signal D·D' are applied to the second AND gate 55 which produces an output signal (C·C')'·D·D' shown in FIG. 12 at the output terminal 56. From the output signal (C·C')'·D·D' the pseudo-defect (c) is cut off and only the true defect (d) is correctly detected.

In this manner the pseudo-defects (b) and (c) have been deleted and the true defects (a) and (d) can be detected by the defect detecting and processing circuit 38.

As explained above the dimensions of portions in the horizontal and vertical directions which have been cut off are determined by the delay times of the first and second delay circuits 52 and 54 and can be set to desired values. As the first delay circuit 52 use may be made of an ultrasonic delay line of glass and the second delay circuit 54 may be formed by an LC circuit.

In the above mentioned embodiment use is made of the pattern scanning optical system shown in FIG. 6, but the present invention is not limited to such a pattern scanning apparatus, but the pattern scanning apparatuses shown in FIG. 5 may be used. In the above embodiment after the video signals obtained by scanning the two patterns 20A and 20B are subtracted, the contour of the defect represented by the difference signal is cut off. It is also possible to cut off the contour of one of the video signals which is to be subtracted in the subtraction circuit by passing said one video signal to the circuit shown in FIG. 10 and then the other video signal is subtracted from this cut off video signal. This can be proved as follows. Now it is assumed that an area of one of the patterns is A and that of the other pattern is B and an amount of cutting off the contour is $\Delta A$, then $(A-\lambda \Delta A)-B=(A-B)-\Delta A$. In this manner it can be apparent that the above two treatments are equivalent to each other.

Figure 13:
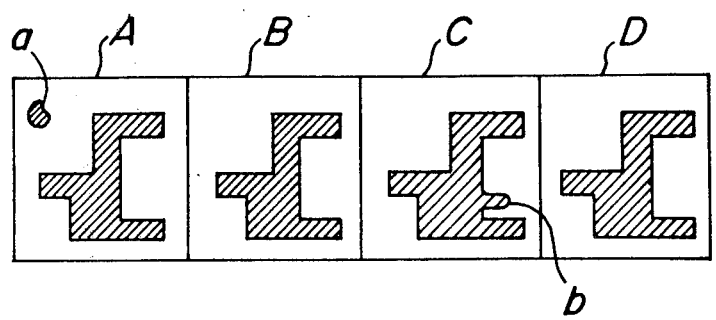
FIG. 13 is a plan view depicting a series of patterns including defects.

According to the present invention it is further possible to identify which pattern between the two patterns which are compared in the circuit 40 includes the detected defect. The basic operational principle of this identification will now be explained with reference to FIG. 13. It is assumed that four patterns A, B, C and D are successively compared to detect defects. In this case the patterns A and C include defects a and b, respectively. In a first comparison of the patterns A and B the defect a is detected, but at this time it is impossible to determine which pattern A or B includes this detected defect a. In a second comparison between the patterns B and C there is no defect at a position at which the defect a has been detected. Then it is decided that the detected defect a is included in the pattern A. During this second comparison a new defect b is detected. However at this time it cannot be certained which pattern B or C includes this detected defect b. This defect b is also detected in a third comparison between the patterns C and D. Then it is determined that the defect b is included in the pattern C. That is to say when a defect is detected in a comparison a position of this detected defect is stored and if a defect is detected in a next comparison at the same position, it is certified that the detected defect is included in the pattern which has been used in the above two successive comparisons. This principle of detecting the defect is based on the fact that a probability of existing defects in successive compared patterns at the same position is very small.

Figure 14:
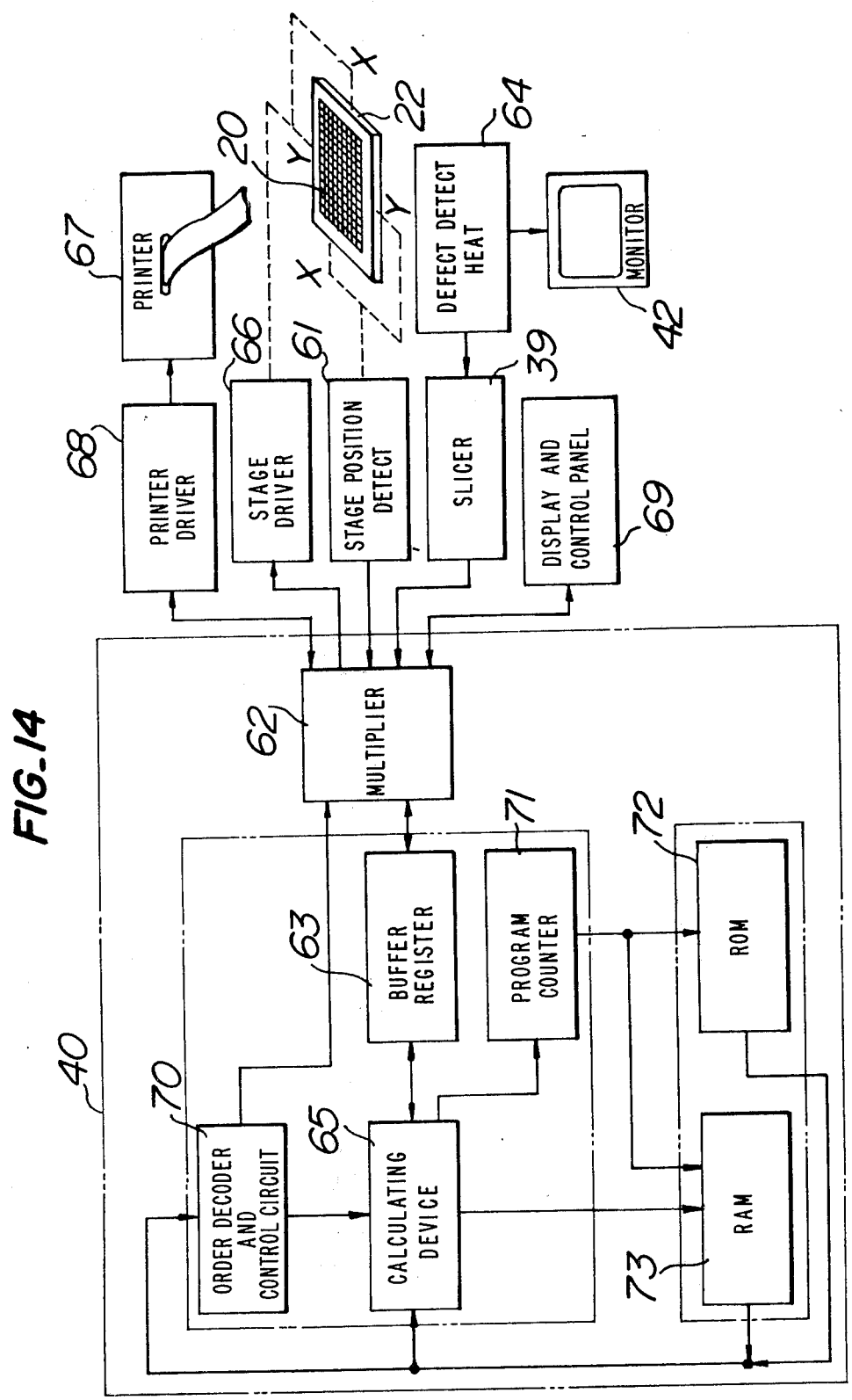
FIG. 14 is a block diagram showing the whole construction of the defect detecting apparatus according to the invention.

FIG. 14 is a block diagram showing an embodiment of the defect detecting and processing circuit 40. In the present embodiment use is made of the scanning apparatus shown in FIG. 6 and the mask 20 to be checked is placed on the carrier stage 22. Two patterns 20A and 20B in this mask are to be compared with each other. As illustrated in FIG. 14 there is provided a stage position detecting device 61 which supplies a signal representing coordinates of the stage 22. This signal is supplied to a register 63 through a multiplier 62. There is further provided a defect detecting head 64 comprising the first and second photoelectric converters 31 and 32 and output signals from this head 64 are supplied through a slicer 39 and the multiplier 62 to the register 63. This register 63 operates as a buffer register and temporary stores data between the multiplier 62 and an operating or calculating device 65. To the multiplier 62 are connected a stage driving circuit 66, a printer 67, a printer driving circuit 68 and a display and control panel 69 by means of which a user can preset various kinds of defect detecting operations.

There are further provided an order decoder and control circuit 70 for controlling the operation of the calculating device 65 and the multiplier 62, a program counter 71 for counting a program address from the calculating device 65, a read only memory 72 for storing contents of programs and a random access memory 73 for storing data from the calculating device 65.

Now the operation of the defect detecting and processing circuit 40 will be explained with reference to a flow chart shown in FIG. 15. The present circuit 40 can effect various operations. An operation for determining which pattern includes a detected defect will be first explained. It is assumed that a mask used manufacturing integrated circuits includes 13×13 chips and each chip is of a rectangular shape having a dimension of 5 mm × 5 mm. In the defect detecting head 64 a single chip is divided into a number of regions of 250μ × 250μ and each region is displayed on the screen of the monitor 42. The single region is further divided into 25 domains each having a dimension of 50μ × 50μ. Therefore in the single chip there are 10,000 domains (100 domains in the horizontal direction and 100 domains in the vertical direction). The stage position detecting device 61 must express each region of a respective chip as X, Y coordinates and the stage driving circuit has to denote each region of a respective chip. Each of 25 domains in a respective region is denoted by a deflection signal for the flying spot cathode ray tube 23. That is to say each of the horizontal and vertical deflection signals is divided into five portions and these signal portions are used as domain denoting signals. In this manner each of 10,000 domains in a respective chip are provided with X and Y coordinates which can be handled in the circuit 40. The stage position detecting device 61 produces such X and Y coordinates.

Before the measurement a distance $d$ between the optical axes of the lenses 27 and 30 is set by means of the display and control panel 69. For example, if two adjacent chips are to be compared with each other, the distance $d$ must be set to 5 mm and if every other chips are to be compared with each other, the distance $d$ has to be set to 10 mm. This setting operation may be carried out by means of a preset counter. The set valve of the distance $d$ is supplied from the panel 69 to the defect detecting and processing circuit 40. In order to adjust the actual distance between the optical axes to the set value the adjusting mechanisms 33 and 34 shown in FIG. 6 are handled with viewing screen of the monitor 42 which displays two pattern images so as to registrate these two images. In the present example the distance $d$ is set to 10 mm.

Figure 16A:
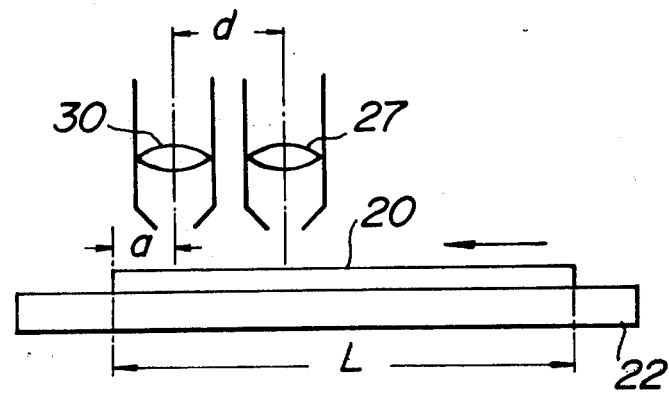
FIGS. 16A to 16C are schematic views showing relative arrangement of the mask and a pair of lenses.
Figure 16B:
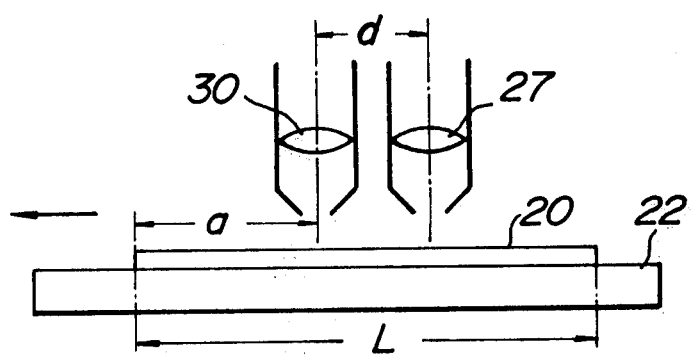
Figure 16C:
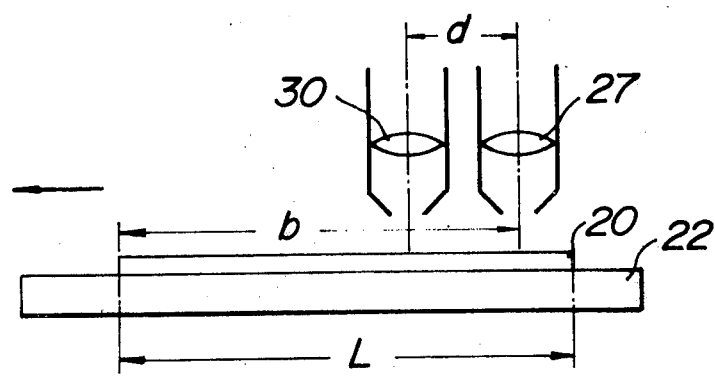

In case of determining which pattern includes the detected defect it is necessary to consider separately the case in which both of two chips to be compared do not situate at a periphery of the mask and the case in which at least one of the two chips situates at the periphery of the mask. FIG. 16 illustrates this situation. In FIG. 16 the stage 22 is to be moved into the left hand as shown by an arrow. Thus the lens 27 is termed as a front lens and the lens 30 as a rear lens. A length of the mask 20 is denoted by L which will be called as a measurement range. In the above example in which the mask has 13×13 chips each having the dimension of 5 mm × 5 mm, the measurement range L amounts to 65 mm. Each chip is represented by 100×100 X, Y coordinates and thus the whole mask is expressed by 1,300×1,300 X, Y coordinates. Now it is assumed that a left hand end of the measurement range L is expressed as a coordinate "0" and a right hand end is expressed as a coordinate "1,300". FIG. 16A illustrates a situation in which a distance $a$ between the optical axis of the rear lens 30 and the left hand end of the measurement range L is smaller than the distance $d$, FIG. 16B shows a situation in which the distance $a$ is longer than the distance $d$ and FIG. 16C depicts a situation in which a sum of a distance $b$ between the optical axis of the front lens 27 and the left hand end of the measurement range and of the distance $d$ is longer than the range L. Therefore in the situation of FIG. 16A a coordinate which is obtained by subtracting the distance $d$ from a coordinate of the optical axis position of the rear lens 30 is far leftward than the left hand edge of the range L and becomes a negative value. In the situation of FIG. 16C a coordinate of the sum of a coordinate of the optical axis of the front lens 27 and the distance $d$ is far rightward than the right hand edge of the range L and becomes a larger value than "1,300".

From the defect detecting head 64 is supplied a signal which represents existence or non-existence of a defect to the defect detecting and processing circuit 40. At the same time from the stage position detecting device 61 the coordinates of the chip being checked is supplied through the register 63 to the calculating device 65. As shown in the flow chart of FIG. 15 the existence or non-existence of defect is first determined. If no defect is detected, the process for this coordinates' position has been completed and the calculating device 65 signals the program counter 71 so as to start a new program cycle. If a defect is detected, the calculating device 65 supplies a signal to the program counter 71 which drives the read only memory 72 so as to read out a program which effects a determination whether a distance = [position of rear lens] − [distance $d$] exceeds the measurement range or not. When it is determined that the above mentioned distance exceeds the measurement range, data for representing that the defect is included at the coordinates of the detected position by the rear lens 30 is stored in the random access memory 73. This program cycle has been ended by this storing process and a similar process is started for a new checking position.

On the contrary when it is determined that the distance of [rear lens position] − [distance $d$] does not exceed the measurement range, the program is further continued and a coordinate of [rear lens position] − [distance $d$] is calculated. Then it is determined whether or not data for expressing that the defect is existent at the calculated coordinate position is stored in the random access memory 73. As the result of this determination if the defect data has been stored at the related position, this defect data in the memory 73 is erased and data indicating that the defect is existent at the coordinate of the rear lens position is newly stored in the memory 73. By this storing procedure this program cycle has been completed and a new program cycle is started.

On the contrary if it is determined that the defect data is not stored at the corresponding coordinate position of [rear lens position] − [distance $d$], it is further determined whether or not a defect data is stored in eight neighbouring domains. By this process if it is determined that the defect data is stored in any one of these domains, the defect data stored at the related position is erased and data expressing that the defect is existent at the coordinate position of the rear lens is newly stored in the random access memory 73. This program cycle has been completed by this storing process.

If it is determined that none of the eight neighbouring domains includes a defect data, it is further checked whether or not a distance = [front lens position] + [distance $d$] exceeds the measurement range. As the result of this checking if said distance does not exceed the measurement range, the defect data is stored at the coordinate position of the rear lens position and the program cycle has been ended.

On the contrary if it is certified that said distance = [front lens position] + [distance $d$] exceeds the measurement range, data expressing that there is a defect at the coordinate position of the front lens is newly stored in the random acess memory 73.

The above program cycles are carried out repeatedly and the defects, coordinates in the relevant chip of the mask 20 can be successively stored in the random access memory 73.

As explained above the defect detecting and processing circuit 40 shown in FIG. 14 can effect various operations with utilizing the information data stored in the above mentioned manner. Next these operations will be explained.

Typing Out the Number of Defects

By operating a button on the control panel 69 the number of defects in each chip is typed out. This is effected by counting the number of defects in each chip stored in the random access memory 73 and supplying this count value to the printer driving circuit 68 through the register 63 and multiplier 62. The driving circuit 68 drives the printer 67 to print out the number of defects.

Display of Overlow of the Number of Defects

As described above in the random access memory 73 the defect data for each chip is stored. If a chip has a number of defects, this chip will be determined as an inferior one. Therefore it is neither necessary nor preferable to store the data of such a number of defects. For example five defects at most can be stored for a single chip and if defects more than five are detected, the defect data is not stored any more. By such a measure the capacity of the memory may be reduced. Upon typing out the defect data such a chip is represented as "overflow".

Skip Scanning for Inferior Chip

As described above if a chip has more than five defects, this chip is identified as an inferior one. If this overlow is detected during the check period, it is not necessary to check this chip further more. In this case the scanning is skipped to a next chip. By this skipping operation the whole checking time may be reduced.

Display of Defect on Monitor Screen

Since the coordinates of the detected defects have been stored in the memory 73, an image of the pattern portion including the defect can be automatically displayed on the screen of the monitor 42 by reading out the coordinates of the related defect and supplying the read out coordinates to the stage driving circuit 66. As explained above this display is effected for each region of the dimension 250$\mu$ × 250$\mu$. Moreover it is possible to denote the particular section which will be displayed on the monitor screen under the control of the panel 69.

By displaying the image of the defect on the monitor, it is possible to check in detail condition and kind of the defects. For example if a dirt applied on the mask has been detected as a mask defect, this dirt is investigated in detail and can be removed. In actual apparatus it is important to check each defect separately in this manner.

Typing Out the Number of Defects for each Row of Chips

As explained above the mask has regular array of chips, i.e. thirteen chips are arranged along each horizontal row. For example, after thirteen chips in the same row have been checked, the number of detected defects can be typed out for each chip and if overflows are detected for more than four chips, the mask is identified as an inferior one and further checking operation for this mask can be deleted. In this manner the checking efficiency may be increased materially.

The present invention is not limited to the embodiments mentioned above, but many modifications are possible within the scope of the invention. For example, in the above embodiment the flying spot scanner, the optical system and the photoelectric converters are fixedly arranged and the patterns are moved with being placed on the carrier stage. It is also possible to arrange the pattern fixedly and move the scanner, the optical system and the photoelectric converters. In the above embodiment the carrier stage may be moved in a stepwise manner instead of in a continuous manner. In the embodiments the photoelectric converters are arranged to receive the light spot passing through the patterns, but they may be arranged to receive the light spot reflected from the patterns. In the above embodiment use is made of the flying spot scanner tube as the device for producing the scanning light spot, but any other devices such as a device using a vibrating mirror may be utilized.

What is claimed is:

1. An apparatus for detecting defects in patterns, particularly defects in chip patterns of photomasks used in manufacturing semiconductor integrated circuits comprising means for producing a scanning light spot;
   an optical system for projecting said scanning light spot simultaneously onto identical portions of two patterns to be compared with each other;
   first and second photoelectric converters each for receiving the light spot passing through or reflected from a respective pattern to produce an output electrical signal; and
   electric circuit means for receiving the output signals from the first and second photoelectric converters and subtracting one of the output signals from the other to produce an output defect signal representing detected defects in the patterns; said circuit means comprising:
   a subtracting circuit for producing a difference signal between the two output signals from the first and second photoelectric converters,
   a delay circuit for delaying the difference signal for a predetermined time period so as to remove pseudo-defects from the output defect signal, and
   circuit means for receiving the delayed difference signal and the non-delayed difference signal and processing them to produce the output defect signal having pseudo-defects deleted therefrom.

2. A defect detecting apparatus according to claim 1, wherein said apparatus further comprises a carrier stage on which a specimen having a number of identical patterns is placed and said optical system is so arranged that two patterns in the specimen are simultaneously scanned by the scanning light spot.

3. A defect detecting apparatus according to claim 2, wherein said scanning light spot producing means comprise a flying light spot cathode ray tube and first and second lenses arranged symmetrically with respect to an axis which passes through a middle point between the two patterns to be compared with each other; whereby the scanning light spot is projected onto one of the patterns by means of said first lens and onto the other pattern by means of said second lens.

4. A defect detecting apparatus according to claim 3, wherein a distance between the first and second lenses is made adjustable.

5. A defect detecting apparatus according to claim 2, wherein said electric circuit means comprise a defect identification circuit which determines to which pattern of the two patterns being compared the detected defect belongs.

6. A defect detecting apparatus according to claim 5, wherein the electric circuit means further comprise a counter for counting the number of the detected defects for each patttern.

7. A defect detecting apparatus according to claim 1, wherein said electric circuit means further comprises a monitor having a screen on which any one of images of the detected defects and the portions of the two patterns is displayed.

8. A defect detecting apparatus according to claim 1, wherein said delay circuit comprises a first delay element for delaying the difference signal for a part of a line period of a raster scanning, a first AND gate for receiving the delayed and non-delayed difference signals; a second delay element for delaying an output signal from the first AND gate for one line period and a second AND gate for receiving the delayed and non-delayed output signal from the first AND gate to produce the defect signal which has not pseudo-defects.

9. An apparatus for detecting defects in patterns, particularly defects in chip patterns of photomasks used in manufacturing semiconductor integrated circuits comprising means for producing a scanning light spot;
an optical system for projecting said scanning light spot simultaneously onto identical portions of two patterns to be compared with each other;
first and second photoelectric converters each for receiving the light spot passing through or reflected from a respective pattern to produce an output electrical signal; and
electric circuit means for receiving the output signals from the first and second photoelectric converters and subtracting one of the output signals from the other to produce an output defect signal representing detected defects in the patterns; said circuit means comprising:
a delay circuit for delaying the output signal from said first photoelectric converter by a predetermined time period;
circuit means for receiving the delayed output signal and the non-delayed output signal from said first photoelectric converter and processing them to produce a composite output signal; and
a subtracting circuit for subtracting the output signal from the second photoelectric converter from the composite output signal of said circuit means so as to produce the output defect signal having pseudo-defects removed therefrom.

10. An apparatus for detecting defects in patterns, particularly defects in chip patterns of photomasks used in manufacturing semiconductor integrated circuits comprising means for producing a scanning light spot;
an optical system for projecting said scanning light spot simultaneously onto identical portions of two patterns to be compared with each other;
first and second photoelectric converters each for receiving the light spot passing through or reflected from a respective pattern to produce an output electrical signal; and
electric curcuit means for receiving the output signals from the first and second photoelectric converters and subtracting one of the output signals from the other to produce a defect signal representing detected defects in the patterns, said electric circuit means including means for determining whether difference signals created by the subtraction of said output signals have a signal width exceeding a predetermined value and for deleting said difference signals from said defect signal if they do not to produce a defect signal having pseudo-defects removed therefrom.

* * * * *